US012595448B2

(12) United States Patent
Taylor, IV et al.

(10) Patent No.: US 12,595,448 B2
(45) Date of Patent: Apr. 7, 2026

(54) SYSTEM AND METHOD USING NANOBUBBLE OXYGENATION FOR MASS PROPAGATION OF A MICROALGAE THAT REMAIN VIABLE IN COLD STORAGE

(71) Applicant: Enlightened Soil Corp, Johns Island, SC (US)

(72) Inventors: George Jesse Taylor, IV, Johns Island, SC (US); Christopher Spaulding, Johns Island, SC (US); Andrew Shuler, Charleston, SC (US); Steve Morton, Hanahan, SC (US)

(73) Assignee: Enlightened Soil Corp, Johns Island, SC (US)

( * ) Notice: Subject to any disclaimer, the term of this patent is extended or adjusted under 35 U.S.C. 154(b) by 799 days.

(21) Appl. No.: 17/869,140

(22) Filed: Jul. 20, 2022

(65) Prior Publication Data

US 2024/0026257 A1 Jan. 25, 2024

(51) Int. Cl.
| | |
|---|---|
| *C12M 1/00* | (2006.01) |
| *A01G 33/00* | (2006.01) |
| *C12M 1/12* | (2006.01) |
| *C12N 1/12* | (2026.01) |

(52) U.S. Cl.
CPC ............. *C12M 21/02* (2013.01); *A01G 33/00* (2013.01); *C12M 23/06* (2013.01); *C12M 31/10* (2013.01); *C12M 43/06* (2013.01); *C12N 1/12* (2013.01)

(58) Field of Classification Search
CPC ...... C12M 21/02; C12M 23/06; C12M 31/10; C12M 43/06; A01G 33/00; C12N 1/12

USPC ...................................................... 435/292.1
See application file for complete search history.

(56) References Cited

U.S. PATENT DOCUMENTS

| | | | |
|---|---|---|---|
| 2008/0299643 A1 | 12/2008 | Howard et al. | |
| 2010/0311157 A1* | 12/2010 | Van Alstyne | C12P 7/649 435/294.1 |
| 2012/0309081 A1* | 12/2012 | Herzog | C12M 29/06 47/1.4 |
| 2015/0196002 A1* | 7/2015 | Friesth | A01K 63/04 315/297 |
| 2019/0216031 A1* | 7/2019 | Hintz | A23K 50/80 |

FOREIGN PATENT DOCUMENTS

| | | |
|---|---|---|
| RU | 2644261 C2 | 2/2018 |

OTHER PUBLICATIONS

Murata et. al., What do patents tell us about microalgae in agriculture?. AMB Expr 11, 154 (2021). pp. 1-12. https://doi.org/10.1186/s13568-021-01315-4.

(Continued)

*Primary Examiner* — Michael L Hobbs
*Assistant Examiner* — Lenora A Abel
(74) *Attorney, Agent, or Firm* — Angelica Colwell; Maynard Nexsen PC

(57) ABSTRACT

A system and method for growing microalgae capable of mixotrophic metabolism, preferably *Chlorella* sp. Microalgae grown in the system using the method are able to survive and grow in dark refrigeration, which allows the algae to be stored and transported for application as a live culture. In addition, the microalgae can be grown in sufficient quantities to be sold commercially for application to crops as a biostimulant.

12 Claims, 3 Drawing Sheets

(56) References Cited

OTHER PUBLICATIONS

Goncalves, Ana. The Use of Microalgae and Cyanobacteria in the Improvement of Agricultural Practices: A Review on Their Biofertilising, Biostimulating and Biopesticide Roles. Applied Sciences. 2021; 11(2):871. p. 1-21. https://doi.org/10.3390/appl11020871.

* cited by examiner

SYSTEM AND METHOD USING NANOBUBBLE OXYGENATION FOR MASS PROPAGATION OF A MICROALGAE THAT REMAIN VIABLE IN COLD STORAGE

BACKGROUND OF THE INVENTION

Rapid population growth following World War II prompted concerns about food security, a limit on the earth's ability to feed growing numbers. Malthusians predicted famine, possibly by the 1990s. This did not happen because of the Green Revolution, an unexpected increase in agricultural efficiency and yield. One element of this was the development of nitrogenous fertilizers, which was in turn a spin-off from munitions technology. Gunpowder factories became fertilizer factories (swords to plowshares).

Synthetic chemical fertilizers make plants grow. However, after seven decades of use there have been unintended consequences such as: 1) declining soil fertility and crop yield stagnation, 2) increasing greenhouse gases, and 3) contamination of groundwater leading to wild algae bloom. The production of synthetic fertilizers requires burning methane; it is estimated that 12% of greenhouse gases originate with modern agriculture, much of that from the use of chemical fertilizers.

In nature, plant growth depends on a symbiotic relationship between plants and soil microorganisms. Plants exude sugars (carbon compounds) from their roots that feed microorganisms present in the soil, in particular bacteria. In return, the soil microorganisms process nutrients needed for plant growth. Soil bacteria convert atmospheric nitrogen to ammonium compounds that can be absorbed by plant roots. This natural process is known as nitrogen fixation, and is primarily a function of bacteria in close contact with roots (this area is known as the "rhizosphere"), and not the work of the plants. Fertile soil in the rhizosphere has as many as 10 billion bacteria per gram. Microbial composition and activity in the soil defines "fertility". Crop rotation is done with legumes to add nitrogen to soil, but it is the bacteria in legume root nodules that fix nitrogen. Other bacteria solubilize phosphorous that is soil-bound.

Chemical fertilizer bypasses the natural process. Over time, microbial activity—fertility—and levels of soil nitrogen and carbon decline. Chemical fertilizers add macronutrients, nitrogen, phosphorous and potassium, to the soil in forms that can be directly absorbed by roots. However, plants absorb just 30% of the nitrogen applied through chemical fertilization. Much of the rest goes into solution, eventually reaching groundwater. It is well-known that the addition of fertilizer to waterbodies, such as is known to occur through farm field runoff into ponds and lakes, promotes the growth of wild algae, leading to harmful algal blooms. In addition, some nitrogen in the fertilizer is converted to nitrous oxide, a potent greenhouse gas. Globally, agriculture accounts for 75% of nitrous oxide released in the atmosphere.

Composted organic material such as manure can be applied to soil to provide nitrogen as well as bacteria and carbon that feeds microbes. However, use of compost is inconvenient because of bulk, and is hard to apply at scale. Processing manure to make organic fertilizers is an industrial process, and there are energy costs with shipping.

Biostimulants provide another way to promote plant growth. Defined in the 2018 U.S. Farm bill, a plant biostimulant (PBS) is a compound or organism that promotes natural processes. A large body of research has shown that live microalgae, in particular *Chlorella vulgaris*, are effective biostimulants through both foliar and soil application. Furthermore, the stimulant effect of microalgae on soil microorganisms is regenerative: application of the microalgae increases organic matter, bacterial mass and soil respiration (a measure of bacterial activity). In other words, application of microalgae improves soil fertility.

SUMMARY OF THE INVENTION

The present invention is a novel approach to inducing heterotrophic metabolic activity in microalgae, meaning that the microalgae grown using the method can consume organic material from medium to grow if placed under conditions where photosynthesis is not possible, i.e., where there is no light. Embodiments of the present invention are directed at improving a method used for growing *Chlorella* sp., preferably *Chlorella vulgaris*, in sufficient quantities to be sold commercially for application to crops as a biostimulant after the algae harvested. In particular, the microalgae grown using the improved method are able to survive dark refrigerated storage and shipment.

Microalgae, and in particular *Chlorella vulgaris*, has been grown for commercial use for decades. A known method for growing microalgae such as *C. vulgaris* at commercial volumes involves photobioreactors (PBR) to maximize growth in limited space.

Most commercial uses of microalgae do not involve live microalgae. For example, when microalgae are grown for oil content (biofuel), or used as an animal feed additive, the algae are processed immediately upon harvesting. In contrast, microalgae used as a PBS must be applied live since the ability of the algae to signal plants and soil microorganisms is the essence of biostimulation. Thus, for commercial use as a PBS, the microalgae must remain viable until application, i.e., during storage and transport.

Microalgae grown by the method taught herein remain viable despite being bottled in the growth medium from the PBR as an "algae concentrate" and stored under refrigeration (6° C.). Refrigeration keeps the concentrate free of contaminants during storage and transport to the site of application because it inhibits growth of common contaminants including protozoans and bacteria. Refrigerated storage is typically dark, which creates a problem for microalgae, because, like higher plants, microalgae are usually autotrophic, meaning that they maintain viability and grow through generation of nutrients by light-dependent photosynthesis:

$$\text{Algae+light+water+}CO_2\text{+inorganic nutrients} \rightarrow \text{Glucose (\& more algae)+}O_2$$

When microalgae are deprived of light photosynthesis stops and the algal cell count falls rapidly (in our laboratory, as much as 50% in five days, then with minimal recovery, Table 1). Thus, with standard methods of propagation, live microalgae have to be produced locally for immediate application as a PBS. This is problematic for widespread commercial use since microalgae are no easy to grow. Studies showing that live microalgae, i.e., locally grown and applied immediately following harvest, are an effective biostimulant. Such studies, applying microalgae grown in PBRs, have been done in northern Africa, southeast Asia, and eastern Europe, but the method has not been adopted in any of these regions because it is difficult to replicate. There has not been a method for growing and storing live microalgae at scale so that it can be grown at one location and distributed to other distant locations for application without colony degradation. The essence of the present invention is a method for growing microalgae, and in particular *Chlorella vulgaris*, that remain viable without a significant decline in cell count while in cold, dark storage due to the induction of heterotrophic metabolism, i.e., microalgae grown by the method are able to consume organic material and grow in the absence of light. This is achieved through hyperoxygenation of the water used in to make the growth medium in the PBR. In the hyperoxygenated environment the microalgae alter metabolic behavior and become "mixotrophic," meaning that though they continue to produce food/energy with photosynthesis while there is light (autotrophic metabolism), they become capable of heterotrophic growth, able to consume organic nutrients, while in the dark. It has been known that algae are capable of heterotrophic feeding, as it has been observed to be induced by the addition of organic nutrients to growth medium. The present method induced heterotrophic metabolism by hyperoxygenation of the growth media, by supersaturating the growth media with oxygen nanobubbles. This has not been reported previously. Nor have there been prior reports of microalgae capable of maintaining algae colony cell count and viability while in dark storage. While this method has been described for growing *C. vulgaris*, it would apply to all *Chlorella* sp. as well as other microalgae capable of mixotrophic metabolism. It would also apply to any other methods that may be used to achieve hyperoxygenated media including, but not limited to, continuous infusion of oxygen or hyperbaric methods.

According to a first embodiment and briefly recited, the method for growing microalgae using the system described herein improves upon a method used to grow microalgae in PBRs. Currently, PBRs are used to grow microalgae in water supplemented with inorganic nutrients. Microalgae grown in this manner can be used processed immediately upon harvest but cannot be transported for application for any use requiring live microalgae cells since the microalgae do not survive dark, refrigerated storage. The improvement described herein comprises an oxygen concentrator having an attached nanobubble generator (NBG). As illustrated in FIG. 1, the inventive system includes an NBG positioned to receive sterilized water from a source. The sterilized water is fed through the NBG to receive nanobubbles of oxygen to increase the measurable oxygen concentration of the water to a saturation of approximately 500%, i.e., a state of hyperoxygenation.

The hyperoxygenated water is then pumped to fill at least one PBR. A well-known mixture of inorganic nutrients widely used for algae production is added to the sterilized water in the PBR to create the growth medium. Then, the PBR is inoculated with microalgae.

The PBRs used in the system are constructed from translucent material so that light from outside the PBR can be used by the microalgae cells growing inside the PBR for photosynthesis. An artificial light source is mounted outside the PBR and simulates a 24-hour day cycle. Since photosynthesis also requires carbon dioxide, a standard aquarium stone bubbler is used to introduce filtered ambient air into the growth medium and keep the microalgae cells in suspension. Upon harvest from the PBR, the microalgae cells are bottled with extracted growth medium as algae concentrate.

An important feature of the improved method is that the microalgae cells it produces are capable of surviving in dark, refrigerated storage for more than six months, which is enough time to allow for transport to an agricultural site for application. The bottled algae concentrate is placed directly into refrigeration (6° C.) for storage prior to sale for use as a biostimulant. The microalgae grown in the system using this method not only remain viable but are able to continue growing while in storage, which maintains the cell count necessary for application for use as an effective biostimulant (see Table 1). The application rate of live algae is 50,000 cells per square foot, applied to soil, foliage or both; as such, one liter of algae concentrate can be diluted to treat 4.5 acres; 5 ml of concentrate treats 1,000 square feet.

Another feature of the improved method is that it allows microalgae to be grown at scale for agricultural use at low cost, requiring minimal engineering, and providing high yield of microalgae in a small space.

These and other features and their advantages will be apparent to those skilled in the art of propagation of microalgae using photobioreactors from a careful reading of the Detailed Description of Preferred Embodiments accompanied by the following drawings.

BRIEF DESCRIPTION OF THE DRAWINGS AND TABLE

Figure 3:
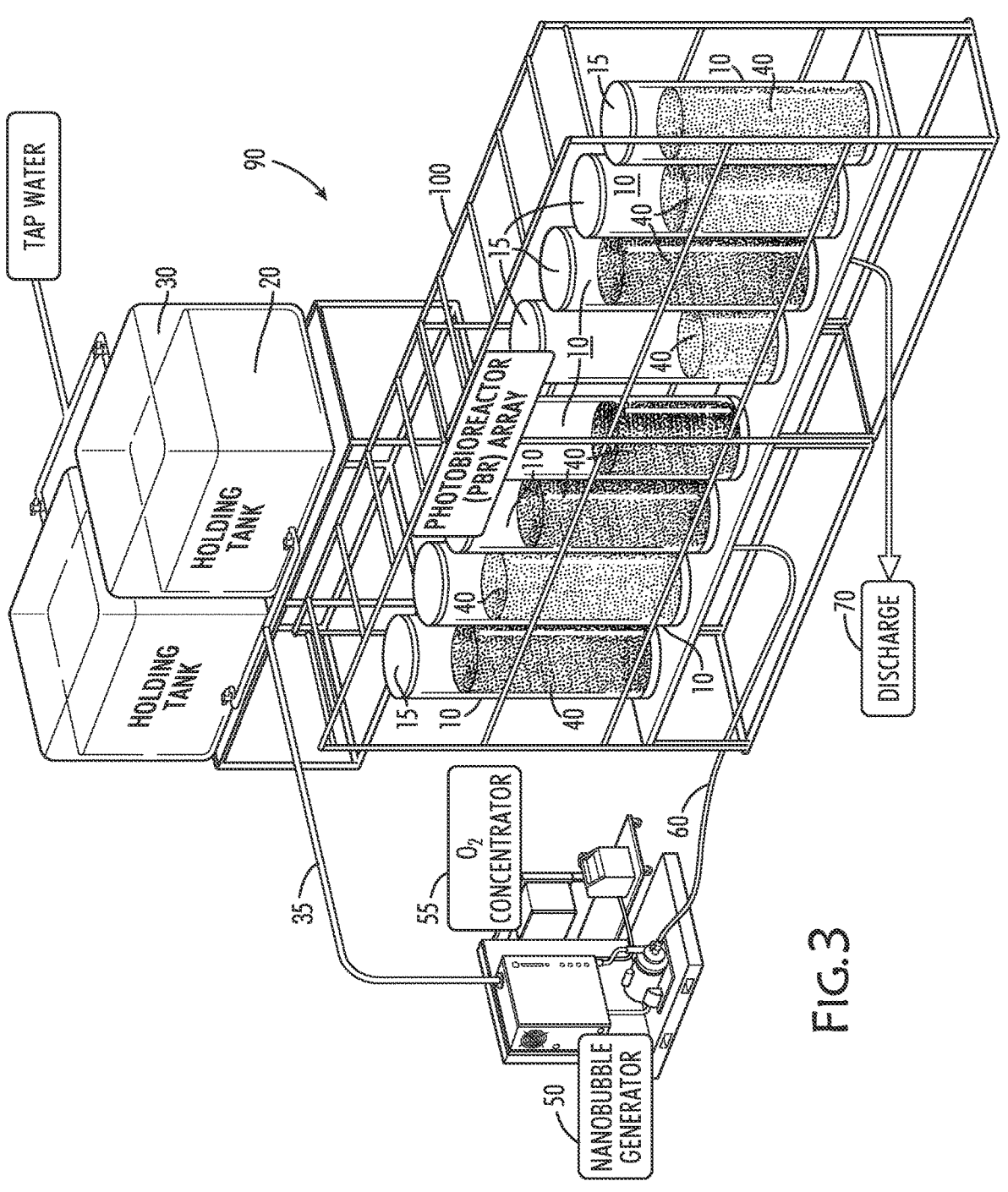

FIG. 3 is a detailed drawing of a preferred embodiment of a growing system (90) improved by addition of a nanobubble generator (NBG) (50) with an attached oxygen concentrator (55), such that an improved method can be used for growth of microalgae. As shown, the growing system (90) uses two holding tanks (30), each having a capacity of 500 gallons (approximately 2000 liters). The holding tanks (30) are positioned higher than the PBRs (10) to allow gravity-feeding of the sterile water to the PBRs (10), after passing it through the nanobubble generator (NBG) (50) with an attached oxygen concentrator (55), to saturate the water with oxygen nanobubbles. Each PBR (10) has a close-fitting, removable lid (15) that can be opened to access the inside of the PBR (40), which allows for the addition of inorganic nutrient solution to the water as well as the algae inoculant once each PBR used in the system is filled. The PBRs (10) in FIG. 3 are shaded to show growth medium (40) containing microalgae, some of which are at a lower level reflecting recent harvest before replenishment of sterilized, hyperoxygenated water and inorganic nutrient solution and reinoculation.

Table 1 compares serial cell counts observed after refrigerated storage of microalgae cultures propagated using the system with oxygen nanobubbles ("Treated") and without oxygen nanobubbles ("Untreated"). Three representative experiments are described in the Table, two with paired controls (A and B), and the third without an untreated control (C).

TABLE 1

Algae cell counts at the time of harvest and later, after a period of dark, refrigerated storage. This compares algae grown using standard commercial methods to EnSoil Algae, grown with proprietary technology that allows continued algae growth while in storage.

| | Cell count at harvest (millions/mL) | Cell count at follow-up (millions/mL) | Cell count: % change |
|---|---|---|---|
| A. Paired samples comparing cell count at harvest and 5 days later. Untreated = normal growing method. Treated = EnSoil Algae using proprietary growing technology | | | |
| Untreated | 12.5 million/mL | 5.2 | −56% |
| Treated | 12.8 | 12.4 | −3% |
| B. Another experiment comparing cell count at harvest and 19 days later. | | | |
| Untreated | 15 | 8.4 | −44% |
| Treated | 16 | 16.8 | +5% |
| C. A third experiment. Cell count of treated algae at harvest and 119 days later. (No untreated control for this experiment.) | | | |
| Treated | 16 | 23.3 | +46% |

DETAILED DESCRIPTION OF PREFERRED EMBODIMENTS

Figure 1:
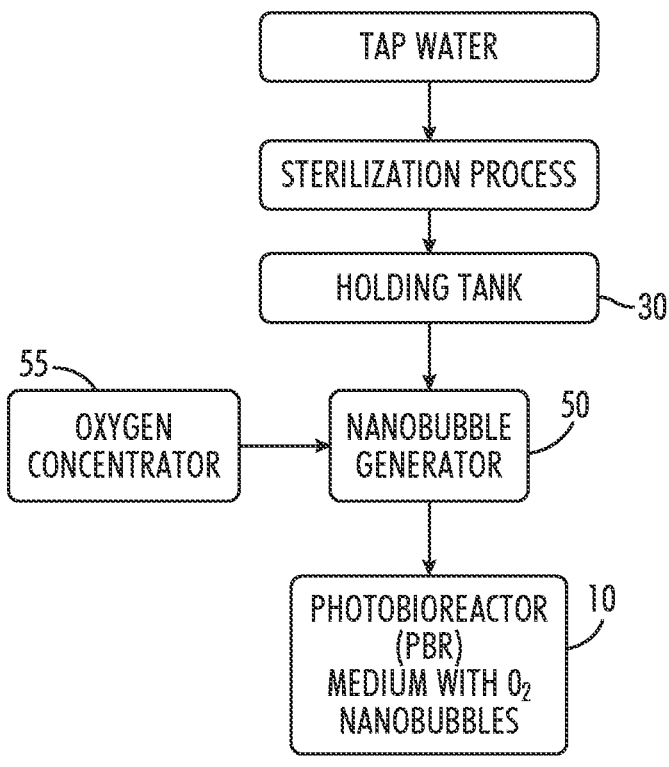
FIG. 1 is a schematic representation of the growing system illustrating the improvement of the system used to grow microalgae using a PBR growing system comprising addition of the NBG and attached oxygen concentrator.

Referring to the drawings, FIG. 1 is a schematic representation of a preferred embodiment of a growing system improved by the addition of an NBG with an attached oxygen concentrator. Preparation of growth medium used to fill each PBR for growing microalgae using the improved method begins with sterilization of water drawn from a municipal source or a well and is not distilled water. The water is sterilized for use in the growing system, which is done by the introduction of ozone to the holding tank, as sometimes used in the commercial production of microalgae.

Sterilized water from the holding tank is gravity fed through a nanobubble generator. An oxygen concentrator is attached to the nanobubble generator to supply oxygen for the creation of oxygen nanobubbles to saturate the sterilized water. At sea level and room temperature, the oxygen content of water in the holding tank is 7 ppm. After addition of oxygen nanobubbles, the oxygen content of water reaching the PBR is at least 50 ppm, with an oxygen saturation of approximately 500%. Following this hyperoxygenation process, the water is then pumped to at least one PBR, a cylindrical container constructed of translucent fiberglass.

Figure 2:
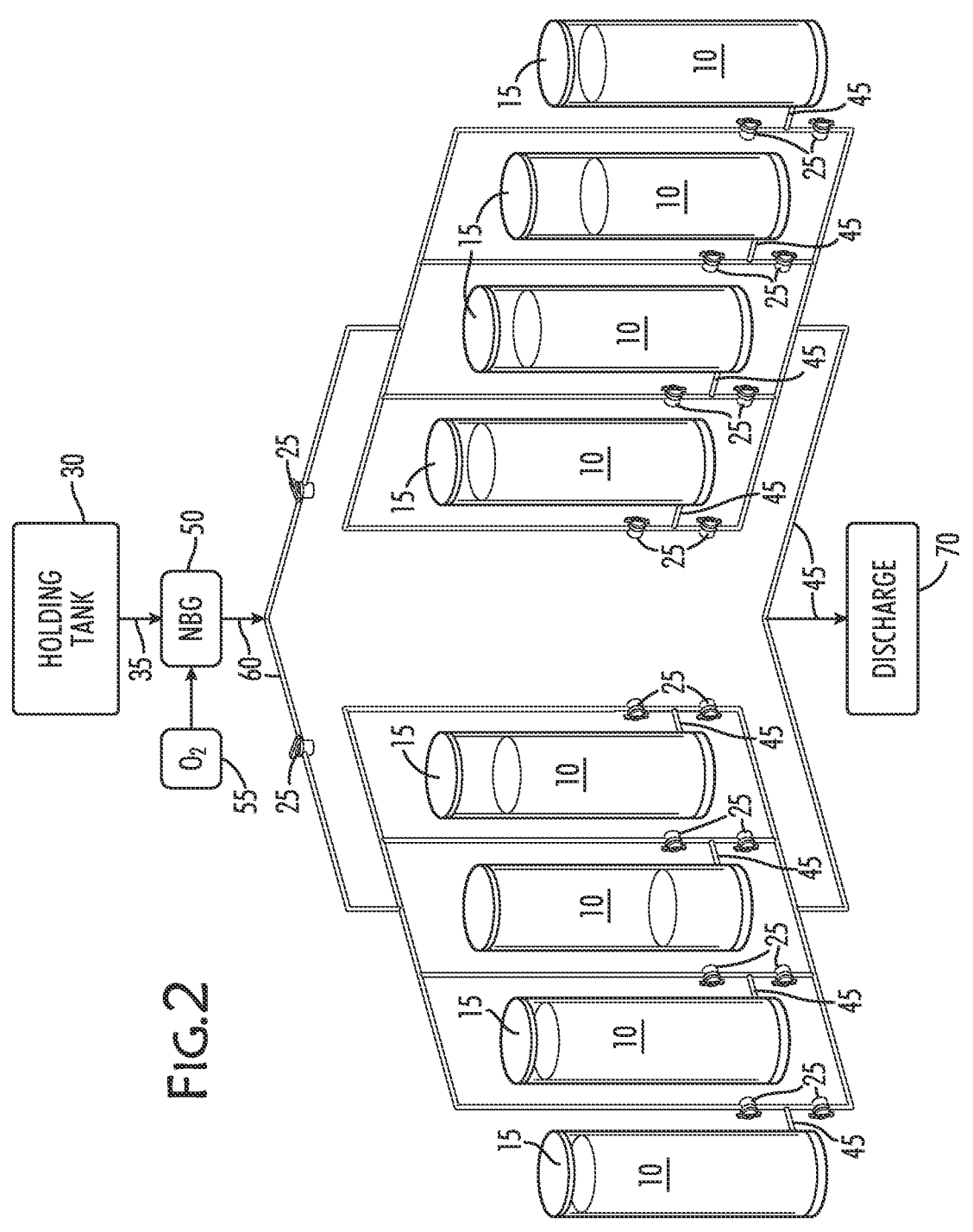
FIG. 2 illustrates a preferred arrangement for eight PBRs (10) plumbed in parallel with valves (25) separating each PBR from others to prevent contamination for a growing system. The valves (25) are also operated to allow filling and harvest of microalgae from individual PBRs from piping at the base of the PBR (45).

FIG. 2 is detailed depiction of eight PBRs (10) plumbed in parallel for use in a growing system. The growing system in depicted in FIG. 3. The PBRs (10) as illustrated each have a capacity of 80 gallons (300 liters). Each PBR (10) carries a fitted, removable lid (15) constructed of the same translucent material, preferably fiberglass, which prevents contamination of the contents by airborne particles or dust, but which can also be removed for access into the PBR.

FIG. 3 is a detailed drawing of a preferred embodiment of a growing system (90) improved by the addition of a NBG (50) with an attached oxygen concentrator (55). FIG. 3 does not depict the plumbing system described in FIG. 2. In this embodiment tap water fills at least one holding tank (30) placed at a higher elevation than the top of the PBRs (10) used in the growing system (90). As described in FIG. 1, sterilized water is gravity-fed from the holding tank (30) through a valve (25) carried on the tank and connected to pipe (35) that is attached to a nanobubble generator or NBG (50). An oxygen concentrator (55) is attached (60) to the NBG (50) to add oxygen to generate oxygen-filled nanobubbles that are injected into the water as it passes through the NBG (50). After receiving the oxygen nanobubbles, the hyperoxygenated water is pumped through tubing (60) connected to the plumbing system illustrated in FIG. 2. By opening and closing the valves the plumbing can be used to fill or drain individual PBRs (10) comprising the production system (90). The plumbing in the growing system (90) consists of polyethylene and stainless steel tubing. As shown in FIG. 2, the plumbing can be arranged to transport the hyperoxygenated water from the nanobubble generator to multiple PBRs plumbed in parallel and separable by valves (25) installed onto the piping that can be opened and closed to fill or drain any individual PBR (10). Both FIGS. 2 and 3 depict PBRs (10) filled with growth medium at different levels of harvest.

As illustrated in FIG. 2, the hyperoxygenated water is introduced through piping connected near the base of each PBR (45). After filling the PBR, inorganic nutrient solution, known in the industry as f/2 or F/2, is added to the sterilized, hyperoxygenated water from the top of the PBR tank by removing the lid (15). At this point the hyperoxygenated growth medium is complete and ready for introduction of algae inoculant.

Immediately after creating the growth medium (40) an algae inoculant, 5 gallons (20 liters) of *Chlorella vulgaris* grown to a cell count of 6-8 million cells/mL is poured into the PBR by removing the lid (15). The *Chlorella vulgaris* strain currently used by the authors was originally purchased from the phycology laboratory at the University of Texas and has been propagated using standard methods.

While not shown in the figures, tubular LED grow lights having a wave length of 440 nM are positioned vertically around each P BR a regular intervals to provide light for photosynthesis. This lighting is set to cycle on for 16 hours and off for 8 hours to simulate a 24-hour day. The inoculated growth medium (40) in the PBR (10) is continuously mixed by introduction of ambient air through an aquarium stone bubbler positioned inside the PBR at the base (not shown in the figures). The stone bubbler is attached by tubing to an external pump mounted outside of the PBR that contains a filter and an air dryer (not shown in the figures). The delivery of ambient air also provides carbon dioxide needed for photosynthesis.

In reference to FIG. 3, growth of the microalgae is monitored over time by drawing samples from the selected PBR (10) from the discharge line (70) attached to the piping (35) connected to each PBR (10) comprising the system (90). Specifically, the valve (25) carried on piping (45) connected to the base of the PBR (10) is opened so that the growth medium and microalgae (40) can be drained from the PBR through the piping (35) for sampling and for harvest. Cells are counted with a hemocytometer or automatic cell counter. Once the cell count in the growth medium (40) exceeds 12 million cells/mL, the culture is a finished "algae concentrate" ready for harvesting, again by opening the valve (25) to drain the desired volume of the through the piping at the base (45) of the PBR (10). A discharge line (70) is connected to the piping to be used for filling polyethylene containers that are placed into refrigerated storage at 6° C. The containers can be any size.

All of the algae concentrate can be harvested from a single PBR tank, or the harvest may be partial, typically drawing 70%-80% of the volume from the PBR. After partial harvest, the volume is replaced with new growth medium (i.e., hyperoxygenated, sterile water to which additional inorganic nutrients may be added). Partial harvest does not require re-inoculation with additional algae culture since the algae remaining in the PBR continue to grow. Typically, the cell count in the PBR recovers to the pre-harvest level in 4-5 days. Thus, with partial harvest, as much as 80% of the PBR's volume can be taken at 5-day intervals. In this case, a PBR can remain in active service for as long as 5 months.

The size of PBRs (10) can vary. The preferred embodiment of the system (90) includes PBRs constructed to 6 feet tall with a capacity of 360 gallons (1350 liters). FIGS. 2 and 3 show the preferred assembly of multiple PBR tanks (10), with FIG. 3 illustrating a photobioreactor array (55) involving eight PBRs (10) held on a rack (100). The rack (100) is constructed of metal, preferably extruded aluminum. The number of individual PBRs that may be used in the PBR array is limited only by available space of the building housing the production system (90). The number of holding tanks can be expanded as well, again depending upon available space of the building.

What is claimed is:

1. A system for growing microalgae comprising:
at least one holding tank and photobioreactor;
a nanobubble generator;
an oxygen concentrator;
a light source;
an aquarium stone bubbler; and
growth medium for growing microalgae within said photobioreactor; wherein said at least one photobioreactor is connected by piping to the second end of tubing carried on said nanobubble generator; wherein said nanobubble generator is removably connected to an oxygen concentrator and also connected by piping to a holding tank for sterilized water that is fed through said nanobubble generator and receives oxygen gas from a supply removably connected to said oxygen concentrator to a level of hyperoxygenation; and wherein once hyperoxygenated, said water is sent through said piping connected to the photobioreactor near a base of said photobioreactor, said piping carrying a first valve positioned above said connection to said photobioreactor and a second valve positioned below said connection to said photobioreactor, for filling said photobioreactor with sterilized, hyperoxygenated water or draining growth medium containing microalgae from said photobioreactor through a length of said piping connected at a second end to a discharge line.

2. The system of claim 1, wherein said holding tank is connected through a valve carried on the tank to a first end of piping, the second end of said piping connected to said nanobubble generator.

3. The system of claim 2, wherein the piping comprises stainless steel.

4. The system of claim 1, wherein said photobioreactor is a cylindrically-shaped container with fixed side walls and bottom and a removable lid, all fabricated from a translucent material.

5. The system of claim 4, wherein said material comprises fiberglass.

6. The system of claim 1, wherein said light source is at least one tubular LED grow light having a wavelength of 44 nm positioned vertically and equidistant around the photobioreactor; said light source operable by a timer set to cycle said light source on for 16 hours and off for 8 hours.

7. The system of claim 1, wherein said growth medium comprises sterilized water hyperoxygenated to an oxygen content of at least 50 ppm through the additional of oxygen filled nanobubbles.

8. The system of claim 1, wherein said oxygen concentrator is removably attached to the nanobubble generator for delivering oxygen gas to the nanobubble generator for filling nanobubbles generated by said generator with oxygen gas.

9. The system of claim 1, wherein the discharge line comprises polyethylene tubing.

10. A method for growing microalgae comprising:
creating growth medium by adding nanobubbles of oxygen to sterilized water by feeding said water through a nanobubble generator removably connected to an oxygen concentrator to receive oxygen gas from a supply removably connected to said oxygen concentrator to hyperoxygenation, or an oxygen level of at least 50 ppm, with an oxygen saturation of approximately 500%;
pumping said sterilized, hyperoxygenated water through tubing connected at one end to said nanobubble generator and at a second end to stainless steel piping plumbed into at least one photobioreactor to fill said photobioreactor with growth medium;
adding inorganic nutrient solution formulated to support microalgal growth to the at least one photobioreactor containing sterilized, hyperoxygenated water to create growth medium and inoculating said growth medium with a substantially homogenous monoculture of microalgae capable of mixotrophic metabolism, having a concentration of 6-8 million cells/mL;
exposing the inoculated growth medium to light for 16 hours at 8 hour intervals;
continuously delivering ambient air through an aquatic stone bubbler carrying a filter placed inside the photobioreactor near a base of the photobioreactor;
monitoring the growth rate of the microalgae by draining a certain volume of said growth medium from the photobioreactor and counting the cells; and
harvesting the microalgae by draining said growth medium containing said microalgae grown to a concentration of 12 million cells/mL into containers, said containers configured to be stored at 6° C.

11. The method of claim 10, wherein the substantially homogenous monoculture of microalgae capable of mixotrophic metabolism is *Chlorella* sp.

12. The method of claim 10, wherein the containers are composed of polyethylene.

* * * * *